US012596130B2

(12) United States Patent
Deshpande

(10) Patent No.: US 12,596,130 B2
(45) Date of Patent: Apr. 7, 2026

(54) DIAGNOSTIC ANALYZER HAVING A DUAL-PURPOSE IMAGER

(71) Applicant: Siemens Healthcare Diagnostics Inc., Tarrytown, NY (US)

(72) Inventor: Manish Deshpande, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 530 days.

(21) Appl. No.: 18/042,847

(22) PCT Filed: Aug. 30, 2021

(86) PCT No.: PCT/US2021/048173
§ 371 (c)(1),
(2) Date: Feb. 24, 2023

(87) PCT Pub. No.: WO2022/051210
PCT Pub. Date: Mar. 10, 2022

(65) Prior Publication Data
US 2023/0324422 A1 Oct. 12, 2023

Related U.S. Application Data

(60) Provisional application No. 63/074,118, filed on Sep. 3, 2020.

(51) Int. Cl.
*G01N 35/00* (2006.01)
*G01N 15/06* (2006.01)
(Continued)

(52) U.S. Cl.
CPC ... *G01N 35/00693* (2013.01); *G01N 15/0612* (2013.01); *G01N 35/00029* (2013.01);
(Continued)

(58) Field of Classification Search
CPC ......... G01N 15/0612; G01N 35/00029; G01N 35/00732; G01N 15/075; G01N 21/8483;
(Continued)

(56) References Cited

U.S. PATENT DOCUMENTS 4,800,164 A 1/1989 Bisconte
5,118,183 A 6/1992 Cargill et al.
(Continued)

FOREIGN PATENT DOCUMENTS

CA 2319731 C 4/2006
CN 109190590 A 1/2019
(Continued)

OTHER PUBLICATIONS

International Search Report and Written Opinion of International Application No. PCT/US2021/048173 dated Dec. 14, 2021.

*Primary Examiner* — Benjamin R Whatley

(57) ABSTRACT

A reagent analyzer comprising an imaging system having a first field of view of a reagent test device and a second field of view of a fluid sample information indicator, and configured to capture a first image depicting the reagent test device and a second image depicting the information indicator; a mirror moveable between a first position outside the first field of view and a second position inside the first field of view and located between the imaging system and the reagent test device, the mirror in the second position reflecting light to produce the second field of view; and a processor executing instructions to: receive the first and second images; analyze the first image to determine calibration information from the information indicator; and analyze the second image to determine constituent presence/absence in the fluid sample applied to the reagent test device, using, in part, the determined calibration information.

8 Claims, 6 Drawing Sheets

(51) Int. Cl.

| | |
|---|---|
| *B01L 3/00* | (2006.01) |
| *G01N 15/075* | (2024.01) |
| *G01N 21/84* | (2006.01) |
| *G01N 33/543* | (2006.01) |

(52) U.S. Cl.
CPC .... *G01N 35/00732* (2013.01); *B01L 3/50855* (2013.01); *B01L 3/5453* (2013.01); *B01L 2300/0825* (2013.01); *G01N 15/075* (2024.01); *G01N 21/8483* (2013.01); *G01N 33/54387* (2021.08); *G01N 2035/00108* (2013.01); *G01N 2035/00752* (2013.01); *G01N 2035/00831* (2013.01)

(58) Field of Classification Search
CPC ... G01N 33/54387; G01N 2035/00108; G01N 2035/00752; G01N 2035/00831; G01N 33/54388; G01N 33/54389; B01L 3/50855; B01L 3/5453; B01L 2300/0825
See application file for complete search history.

(56) References Cited

U.S. PATENT DOCUMENTS

| | | | |
|---|---|---|---|
| 5,955,736 A * | 9/1999 | Robinson | G01N 21/6452 |
| | | | 250/461.1 |
| 6,493,097 B1 | 12/2002 | Ivarsson | |
| 7,264,971 B2 | 9/2007 | Stock | |
| 8,128,871 B2 | 3/2012 | Petruno et al. | |
| 8,321,055 B2 | 11/2012 | Chen et al. | |
| 8,382,812 B2 | 2/2013 | Kang et al. | |
| 9,210,288 B2 | 12/2015 | Bridges et al. | |
| 9,235,744 B2 | 1/2016 | Hensel et al. | |
| 9,251,393 B2 | 2/2016 | Pollack | |
| 9,373,017 B2 | 6/2016 | Liu et al. | |
| 9,439,630 B2 | 9/2016 | Zimmerle et al. | |
| 9,474,476 B2 | 10/2016 | Ishimaru | |
| 9,618,620 B2 | 4/2017 | Zweigle et al. | |
| 9,870,498 B2 | 1/2018 | Reynolds et al. | |
| 10,114,020 B2 | 10/2018 | Dunn et al. | |
| 10,132,743 B2 | 11/2018 | Enigk et al. | |
| 10,249,214 B1 | 4/2019 | Novotny et al. | |
| 2011/0293153 A1 | 12/2011 | Plickert et al. | |
| 2012/0270305 A1 | 10/2012 | Reed et al. | |
| 2013/0203627 A1 | 8/2013 | Moll et al. | |
| 2016/0020986 A1 | 1/2016 | Bosko et al. | |
| 2016/0370366 A1 * | 12/2016 | Fleming | B01L 3/502746 |
| 2017/0289412 A1 | 10/2017 | Staker et al. | |
| 2018/0196037 A1 | 7/2018 | Polwart et al. | |
| 2018/0259453 A1 | 9/2018 | Booker et al. | |
| 2019/0287271 A1 | 9/2019 | Kisner et al. | |
| 2020/0242809 A1 * | 7/2020 | Limburg | G01N 21/93 |

FOREIGN PATENT DOCUMENTS

| | | |
|---|---|---|
| GB | 1579188 A | 11/1980 |
| WO | 2013064561 A1 | 5/2013 |
| WO | 2019215199 A1 | 11/2019 |
| WO | 2020016616 A1 | 1/2020 |

* cited by examiner

DIAGNOSTIC ANALYZER HAVING A DUAL-PURPOSE IMAGER

This application claims benefit under 35 USC § 119(e) of U.S. Provisional Application No. 63/074,118, filed Sep. 3, 2020. The entire contents of the above-referenced patent application(s) are hereby expressly incorporated herein by reference.

BACKGROUND

To satisfy the needs of the medical profession as well as other expanding technologies, such as the brewing industry, chemical manufacturing, etc., a myriad of analytical procedures, compositions, and tools have been developed, including the so-called "dip-and-read" type reagent test devices. Regardless of whether dip-and-read test devices are used for the analysis of a biological fluid or tissue, or for the analysis of a commercial or industrial fluid or substance, the general procedure involves a test device coming in contact with the sample or specimen to be tested, and manually or instrumentally analyzing the test device.

A lateral flow immunoassay is a diagnostic device used to confirm the presence or absence of a target analyte. Lateral flow immunoassays typically contain a flow path which conveys a sample past a control line position and a test line position. A control line at the control line position confirms the test is working properly, and a test line at the test line position provides the result of the lateral flow immunoassay. Lateral flow immunoassays are developed to be used in a dipstick format or in a housed test format. Both dipsticks and housed tests work in a similar way, and generally fall within one of two categories: sandwich assays in which a positive test is represented by the presence of a coloured line at the test line position; and competitive assays in which a positive test is represented by the absence of a coloured line at the test line position.

Dip-and-read reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a dip-and-read reagent test device into a sample of body fluid or tissue, such as urine or blood, and observing a detectable response, such as a change in color or a change in the amount of light reflected from, or absorbed by, the test device.

Many of the dip-and-read reagent or lateral flow immunoassay test devices for detecting body fluid components are capable of making quantitative, or at least semi-quantitative, measurements. Thus, by measuring the detectable response after a predetermined time, a user can obtain not only a positive indication of the presence of a particular constituent in a test sample, but also an estimate of how much of the constituent is present. Such dip-and-read reagent or lateral flow immunoassay test devices provide physicians and laboratory technicians with a facile diagnostic tool, as well as with the ability to gauge the extent of disease or bodily malfunction.

Illustrative of dip-and-read reagent test devices currently in use are products available from Siemens Healthcare Diagnostics Inc., under the trademark MULTISTIX, and others. Immunochemical, diagnostic, or serological test devices, such as these usually include one or more carrier matrix, such as absorbent paper, having incorporated therein a particular reagent or reactant system which manifests a detectable response (e.g., a color change in the visible or ultraviolet spectrum) in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the dip-and-read reagent test device with a sample is indicative of the presence of a particular constituent and/or its concentration in the sample. Some other examples of dip-and-read reagent test devices and their reagent systems may be found in U.S. Pat. Nos. 3,123,443; 3,212,855; and 3,814,668, the entire disclosures of which are hereby incorporated herein by reference.

Similarly, lateral flow immunoassay devices currently in use include products from Siemens Healthcare Diagnostics Inc., under the trademark Clinitest hCG for example. These test devices accept a urine sample into the flow path in a housed test wherein the sample flows past a control and a test line and provide an indication of the presence of hCG in the sample.

However, dip-and-read reagent and lateral flow immunoassay test devices suffer from some limitations. For example, dip-and-read reagent test devices typically require a technician to manually dip the test device into a sample, wait for a prescribed amount of time, and visually compare the color of the test device to a color chart provided with the test device. This process is slow and the resulting reading is highly skill-dependent (e.g., exact timing, appropriate comparison to the color chart, ambient lighting conditions, and technician vision) and may be inconsistent between two different technicians performing the same test. Finally, the act of manually dipping the test device into the sample may introduce cross-contamination or improper deposition of the test sample on the test device, such as via incomplete insertion of the test device into the sample, insufficient time for the sample to be deposited onto the test device, or having too much sample on the test device which may drip, leak, or splash on the technician's work area, person, or clothing.

Testing tools and methods have been sought in the art for economically and rapidly conducting multiple tests, especially via using automated processing. Automated analyzer systems have an advantage over manual testing with respect to cost per test, test handling volumes, and/or speed of obtaining test results or other information.

Automated instruments (e.g., CLINITEK STATUS reflectance photometer, manufactured and sold by Siemens Healthcare Diagnostics, Inc.) which are currently available for instrumentally reading individual dip-and-read reagent or lateral flow immunoassay test devices, which may be referred to herein as reagent strips, require each dip-and-read reagent test device to be manually loaded into the automated instrument after contacting the test device with the specimen or sample to be tested. Manual loading requires that the reagent test device be properly positioned in the automated instrument within a limited period of time after contacting the solution or substance to be tested. At the end of the analysis, used test devices are removed from the instrument and disposed of in accordance with applicable laws and regulations.

Another development is the introduction of multiple-profile reagent cards and multiple-profile reagent card automated analyzers. Multiple-profile reagent cards are essentially card-shaped test devices which include multiple reagent-impregnated matrices or pads for simultaneously or sequentially performing multiple analyses of analytes, such as the one described in U.S. Pat. No. 4,526,753, for example, the entire disclosure of which is hereby incorporated herein by reference. The reagent pads on the multiple-profile reagent card are typically arranged in a grid-like arrangement and spaced at a distance from one another so as to define several rows and columns of reagent pads. Adjacent reagent pads in the same row may be referred to as a test strip, and may include reagents for a preset combination of tests that is ran for each sample, for example.

Multiple-profile reagent cards result in an efficient, economical, rapid, and convenient way of performing automated analyses. An automated analyzer configured to use multiple-profile reagent cards typically takes a multiple-profile reagent card, such as from a storage drawer, or a cassette, and advances the multiple-profile reagent card through the analyzer over a travelling surface via a card moving mechanism, typically one step at a time so that one test strip (or one row of reagent pads) are positioned at a sample-dispensing position and/or at one or more read position. Exemplary card moving mechanisms include a conveyor belt, a ratchet mechanism, a sliding ramp, or a card-gripping or pulling mechanism. As the multiple-profile reagent card is moved or travels along the travelling surface and is positioned at the sample-dispensing position, one or more pipettes (e.g., manual or automatic) deposits a volume of one or more samples on one or more of the reagent pads on the reagent card. Next, the reagent pads are positioned at one or more read positions and analyzed (e.g., manually or automatically) to gauge the test result. The reagent card is placed in the field of view of an imaging system, such as an optical imaging system, a microscope, or a photo spectrometer, for example, and one or more images of the reagent pads on the card (e.g., optical signals indicative of the color of the reagent pads) is captured and analyzed. Typically, the field of view of the imaging system is relatively large to allow for the capture of multiple images of the same reagent pad as the reagent card is moved or stepped across multiple read positions in the field of view of the imaging system. The field of view encompasses multiple read positions or locations, and each reagent pad is moved in a stepwise fashion through the read positions as the reagent card travels across the field of view of the imaging system. Because the analyzer moves the card between various read positions in known intervals of time, the multiple images taken in the field of view of the imaging system allow the analyzer to determine changes in the color of the reagent pad as a result of the reagent pad reacting with the sample at each read position as a function of the time it takes the pad to be moved to the respective read position, for example. Finally, the used card is removed from the analyzer, and is disposed of appropriately.

In some instances, a barcode provided on a sample container containing the sample is scanned by the analyzer to obtain calibration information that can be used by a processor within the analyzer to determine a presence or concentration of an analyte of interest within the sample. Such analyzers, however, require two imagers with each analyzer, the two imagers each having a distinct field of view, one for reading the barcode and another one for reading the test device. The presence of two imagers adds additional cost and complexity in the construction of the analyzers.

There is a need to reduce the cost and complexity of the analyzers. It is to such an improved analyzer that the inventive concepts disclosed herein are directed.

SUMMARY

The inventive concepts disclosed herein generally relate to a diagnostic analyzer for determining a presence and/or concentration of at least one analyte of interest within a sample contacting a reagent on a test device, and more particularly, but not by way of limitation, to an analyzer having an imager with a first field of view and a second field of view. The imager obtains first information from the first field of view, and second information from the second field of view. The first and second information are passed to a processor configured to determine the presence and/or concentration of the analyte of interest using the first information and, in some implementations, the second information.

In one aspect of the present disclosure, the first field of view may be configured to encompass at least a portion of a reagent test device and the second field of view may be configured to encompass an information indicator, such as a barcode or other information descriptor, of a sample vessel and/or of a reagent test device, the first field of view different than the second field of view.

In one aspect of the present disclosure, an exemplary reagent analyzer may comprise: a sample tray configured to hold a reagent test device with a portion of a fluid sample applied to the reagent test device; an imaging system having a first field of view and a second field of view, the first field of view encompassing at least a portion of the reagent test device held in the sample tray, the second field of view encompassing an information indicator on a sample vessel holding the fluid sample and/or on the reagent test device, the imaging system configured to capture a first image having pixels using the first field of view and to capture a second image having pixels using the second field of view, the first image depicting at least a portion of the reagent test device and the second image depicting the information indicator; a mirror moveable between a first position outside of the first field of view of the imaging system and a second position inside the first field of view of the imaging system, the second position located between the imaging system and the sample tray, the mirror in the second position reflecting light to produce the second field of view to the imaging system to capture the second image; and a computer processor executing instructions that cause the computer processor to: receive the first image and the second image; analyze the pixels of the first image to determine calibration information from the information indicator for analyzing the fluid sample and/or to determine other information; and analyze the pixels of the second image to determine a presence or an absence of a target constituent being in the fluid sample applied to the reagent test device. The analysis of the pixels of the second image may use, in part, the determined calibration information.

In one aspect of the present disclosure, an exemplary method may comprise: moving a mirror from a first position to a second position, the first position outside of a first field of view of an imaging system and the second position inside the first field of view of the imaging system, the second position located between the imaging system and a sample tray configured to hold a reagent test device with a portion of a fluid sample applied to the reagent test device, the mirror in the second position reflecting light to produce a second field of view to the imaging system; positioning an information indicator on a sample vessel containing the fluid sample and/or on the reagent test device in the second field of view of the imaging system, the barcode indicative of calibration information for use in analyzing the fluid sample; capturing, with the imaging system using the second field of view, an information image having pixels, the information image depicting the information indicator; moving the mirror from the second position to the first position; positioning the reagent test device in the sample tray in the first field of view of the imaging system; capturing, with the imaging system using the first field of view, a device image having pixels, the device image depicting at least a portion of the reagent test device; analyzing, with a computer processor executing processor executable code stored in a non-transitory computer readable medium, the pixels of the information image to determine the calibration information for the fluid sample from the information indicator; and analyzing, with the computer processor executing processor executable code stored in a non-transitory computer readable medium, the pixels of the device image to determine a presence or an absence of a target constituent being in the fluid sample applied to the reagent test device. The analysis of the pixels of the device image may use, in part, the determined calibration information.

In one aspect of the present disclosure, an exemplary reagent analyzer may comprise: an imaging system having a first field of view and a second field of view, the first field of view positioned to encompass at least a portion of a reagent test device, the second field of view positioned to encompass an information indicator on a fluid sample and/or on the reagent test device, the imaging system configured to capture a first image having pixels using the first field of view and to capture a second image having pixels using the second field of view, the first image depicting at least a portion of the reagent test device and the second image depicting the information indicator; a mirror moveable between a first position outside of the first field of view of the imaging system and a second position inside the first field of view of the imaging system, the second position located between the imaging system and the reagent test device, the mirror in the second position reflecting light to produce the second field of view to the imaging system to capture the second image; and a computer processor executing instructions that cause the computer processor to: receive the first image and the second image; analyze the pixels of the first image to determine calibration information from the information indicator for analyzing the fluid sample; and analyze the pixels of the second image to determine a presence or an absence of a target constituent being in the fluid sample applied to the reagent test device. The analysis of the second image may use, in part, the determined calibration information.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals are intended to refer to the same or similar elements for consistency. For purposes of clarity, not every component may be labeled in every drawing. Certain features and certain views of the figures may be shown exaggerated and not to scale or in schematic in the interest of clarity and conciseness. In the drawings.

DETAILED DESCRIPTION

Figure 1:
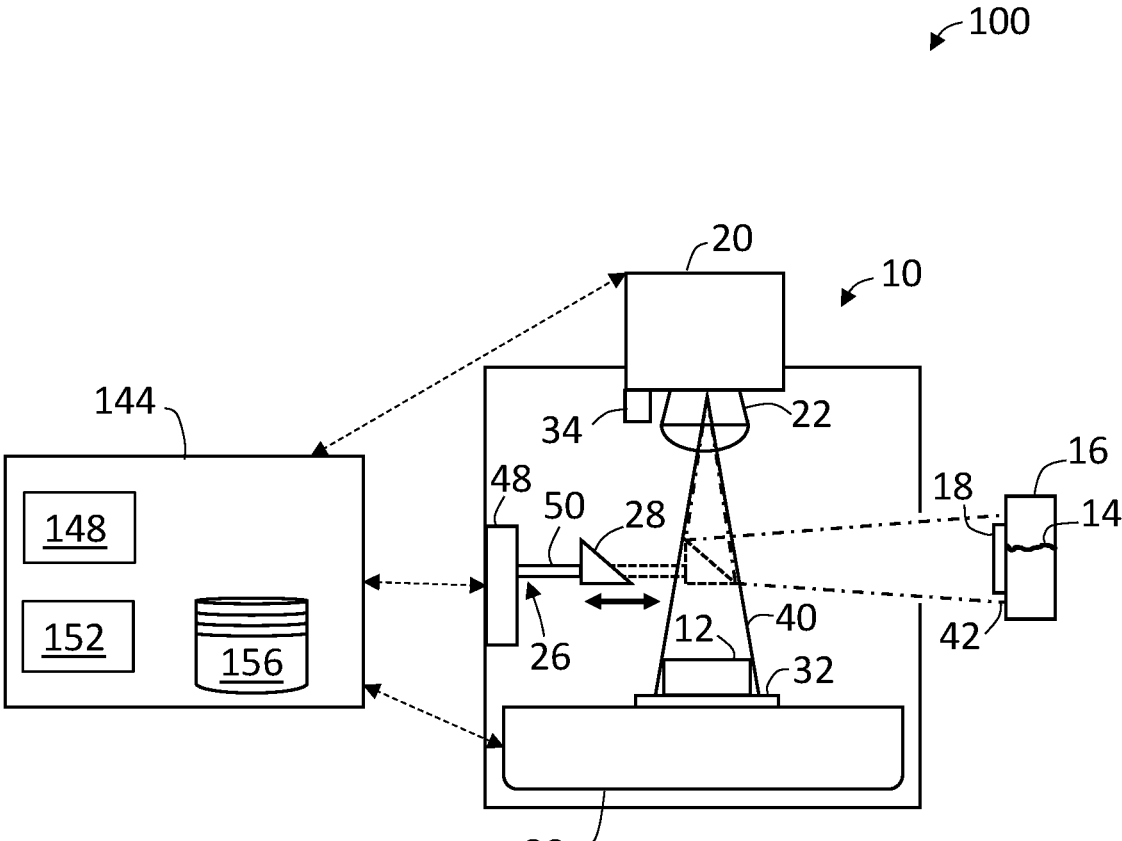
FIG. 1 is a front elevation view of an exemplary embodiment of an analyzer system in accordance with the present disclosure, showing a mirror in a first position and a reagent test device positioned in a first field of view of an imaging system thereof.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts disclosed herein may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein "reagent test device" may refer to dip-and-read reagent test device(s) and/or multiple-profile reagent card(s); including pad(s), reagent pad(s), reagent strip(s), and/or test strip(s).

As used herein "dry reagent test device," "dry pad," "dry reagent pad," or "dry test strip" refer to a reagent test device or a row of reagent test devices which does not have a volume of sample deposited thereon, or that does not have a sufficient amount of sample deposited thereon to react with the reagent. For example, a dry reagent pad can be the unreacted reagent pad prior to dispensing a volume of sample thereon.

As used herein "wet reagent test device," "wet pad" or "wet reagent pad" refer to a reagent test device that has a volume of sample deposited thereon such that the reagent in the reagent test device may react with its target constituent if such constituent is present in the sample. A wet test device may also have a volume of a negative control deposited thereon.

Finally, as used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, computational error, rounding error, and combinations thereof, for example.

The inventive concepts disclosed herein are generally directed to diagnostic analyzers for determining a presence and/or concentration of at least one analyte of interest within a sample contacting a reagent on a reagent test device, and more particularly, but not by way of limitation, to an analyzer having an image system with a first field of view for determining the analyte(s) of interest in a sample and a second field of view provided in conjunction with a moveable mirror to encompass an information indicator, such as a barcode or other depiction, containing calibration information for the sample and/or the reagent test device. While the inventive concepts disclosed herein will be described primarily in connection with analyzers using dip-and-read reagent test device(s), the inventive concepts disclosed herein are not limited to automatic or manual analyzers or to dip-and-read reagent test devices or multiple-profile reagent cards. For example, a method according to the inventive concepts disclosed herein may be implemented with a manual analyzer, or may be implemented with an automatic analyzer using a dip-and-read reagent test device, or a reel of reagent test devices on a substrate, or automatic analyzers using multiple-profile reagent cards or cassettes, and/or combinations thereof, as will be appreciated by a person of ordinary skill in the art having the benefit of the instant disclosure.

Figure 2:
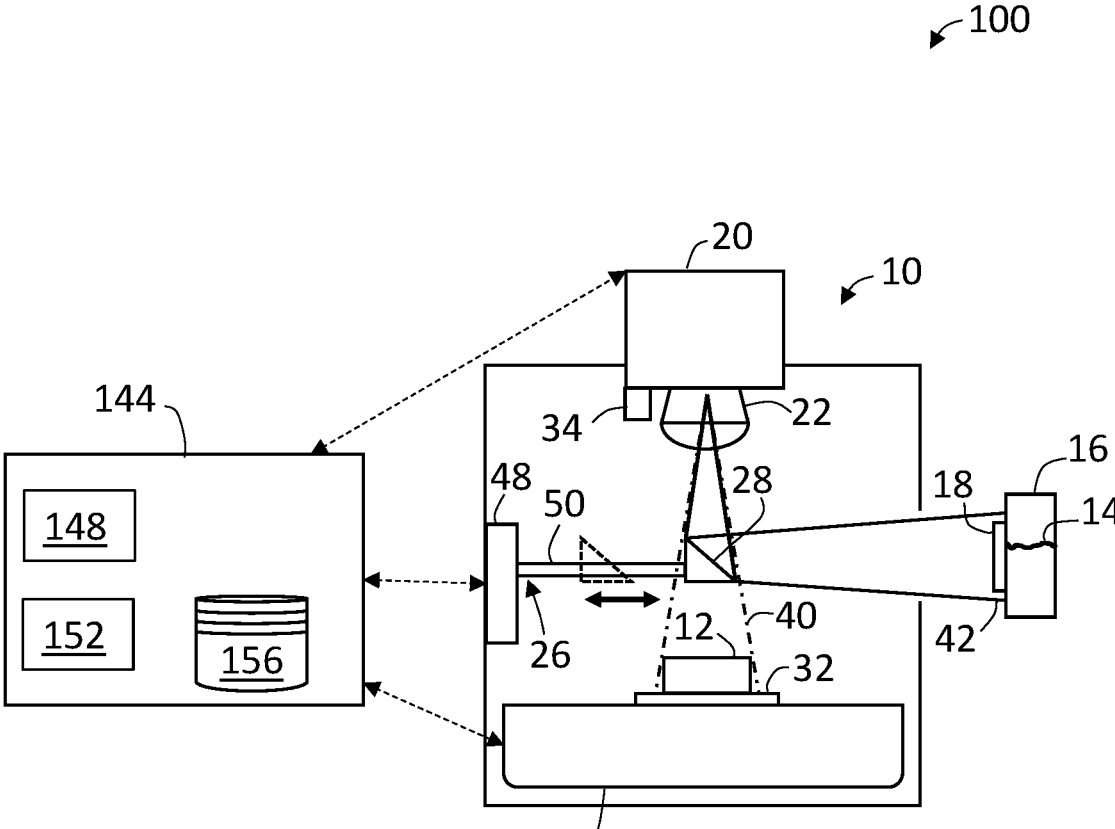
FIG. 2 is a front elevation view of the analyzer system of FIG. 1, showing the mirror in the second position and a barcode positioned in a second field of view of the imaging system.
Figure 3:
FIG. 3 is a front elevation view of an exemplary embodiment of an analyzer system in accordance with the present disclosure.
Figure 3:
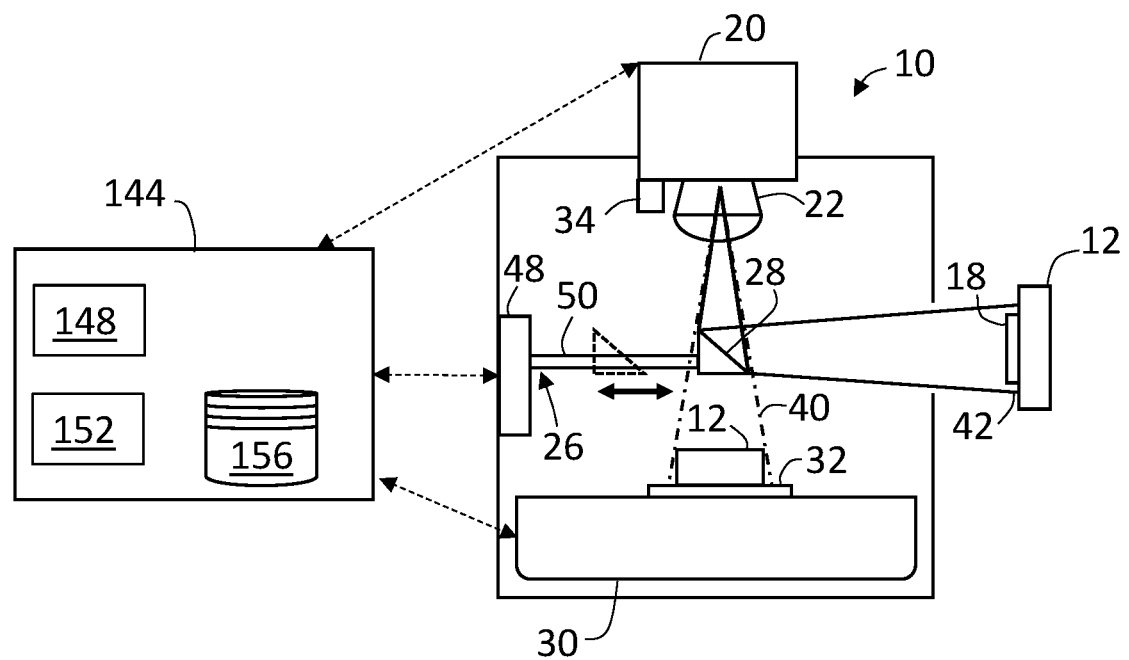

Referring now to FIGS. 1-3, shown therein is an exemplary embodiment of an analyzer system 100 having a reagent analyzer 10 according to the inventive concepts disclosed herein. The reagent analyzer 10 may be configured to analyze one or more reagent test device 12. For example, the reagent analyzer 10 be a dip-and-read reagent test device analyzer or an automatic reagent card analyzer or a lateral flow immunoassay analyzer. Exemplary embodiments of automatic reagent card analyzers are described in detail in U.S. patent application Ser. No. 13/712,144, filed on Dec. 12, 2012, now U.S. Pat. No. 9,606,103, issued Mar. 28, 2017; and in PCT application No. PCT/US2012/069621, filed on Dec. 14, 2012, the entire disclosures of which are hereby expressly incorporated herein by reference.

One or more fluid sample 14 may be provided for testing with the reagent analyzer 10. The fluid sample 14 may be any bodily fluid, tissue, or any other chemical or biological sample, and combinations thereof, such as urine, saliva, or blood, for example. The fluid sample 14 may be in liquid form and may contain one or more target constituents such as bilirubin, ketones, glucose, or any other desired target constituent, for example.

Figure 4:
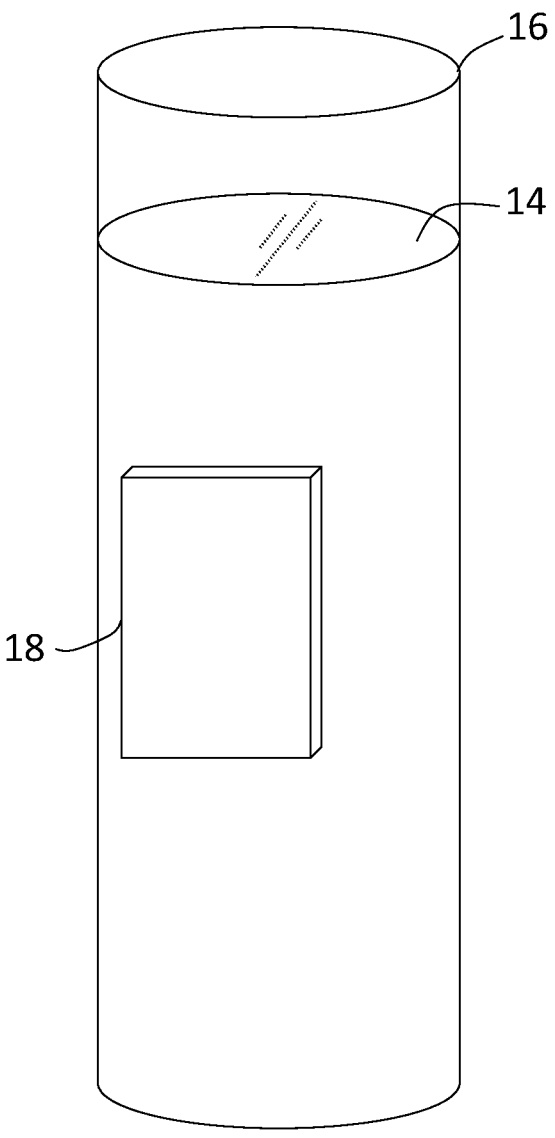
FIG. 4 is a perspective view of an exemplary sample vessel and barcode in accordance with one aspect of the disclosure.

As shown in FIGS. 1, 2, and 4, the one or more fluid sample 14 may be contained in a sample vessel 16. The sample vessel 16 may be a bottle, vial, or other container. The sample vessel 16 may have one or more information indicator 18 located on the sample vessel 16. The information indicator 18 may be located on the outside of the sample vessel 16, for example.

The reagent test device 12 may be a wet reagent test device with a portion of the fluid sample 14 applied to the reagent test device 12. As shown in FIG. 3, in some implementations, the information indicator 18 may be located on the reagent test device 12.

The information indicator 18 may comprise one or more barcode, alphanumeric characters, other character, icon, chemical indicator (e.g. thermal dots or other thermal label), or other information-carrying depictions. In one embodiment, the information indicator 18 may be a one-dimensional barcode or two-dimensional barcode or other type of barcode.

In some implementations, the information indicator 18 may contain information indicative of calibration information for the fluid sample 14. In general, the calibration information may include coefficients for use in the conversion of the measured image values into analytical results. The calibration information may include specific information about the chemistry. The calibration information may include one or more of: information about what specific assay is being analyzed, information that allows conversion of image specific values to analytical results (which may be lot specific), reagent type information to define which reagent(s) is being used, region specific information that gives region specific output and/or confirms validity of the test in the region, expiry information (for example, when there are shelf-life limitations), environmental excursion indicators (for example, when there are concerns of performance based on exposure to conditions outside of claimed).

Generally, the reagent analyzer 10 may include an imaging system 20 comprising one or more image sensor such as a camera 22, a mirror system 26 having a mirror 28 moveable between at least a first position (FIG. 1) and a second position (FIGS. 2 and 3), and a sample tray 30 configured to hold the one or more reagent test device 12. In one embodiment, the reagent analyzer 10 may comprise one or more illumination source 34 positioned to illuminate the one or more reagent test device 12 when the one or more reagent test device 12 is positioned in the sample tray 30.

In one embodiment, the imaging system 20 may be fixed at, or movable to, a relative distance from the sample tray 30, for example. The imaging system 20 and/or the camera 22 may include one or more lens with a focal length selected to provide a first field of view 40 (which may also be referred to herein as a device field of view 40) to include at least a portion of the sample tray 30 such that one or more portion of the reagent test device 12 is within the first field of view 40 when the mirror 28 is in the first position, and to provide a second field of view 42 (which may also be referred to herein as an information field of view 42) to include the information indicator 18 on the sample vessel 16 and/or on the reagent test device 12 (for example, before the reagent test device 12 is loaded on the sample tray 30 and/or to include another portion of the reagent test device 12 having the information indicator 18 once the reagent test device 12 is loaded on the sample tray).

The first field of view 40 is different than the second field of view 42. In some implementations, the first field of view 40 does not overlap with the second field of view 42. In some implementations, the first field of view 40 partially, but not completely, overlaps with the second field of view 42.

The imaging system 20 may be implemented and function as a reader, and may be supported at a location at a relative distance from the sample tray 30, such as above the sample tray 30, or other suitable location, such that the first field of view 40 of the imaging system 20 includes at least a portion of the sample tray 30 such that one or more portion of the reagent test device 12 is within the first field of view 40 when the mirror 28 is in the first position. The imaging system 20 may be configured to detect or capture a first image or a first optical signal indicative of a reflectance value or a color value of one or more portion of the reagent test device 12 positioned in the first field of view 40 of the imaging system 20. The imaging system 20 may be configured to detect or capture a second image or a second optical signal indicative of the information indicator 18 in the second field of view 42 of the imaging system 20.

The first image may be taken at a first instance of time and the second image may be taken at a second instance of time. The first instance of time may be before or after the second instance of time.

The camera 22 of the imaging system 20 may include any desired digital or analog imager, such as a digital camera, an analog camera, a CMOS imager, a diode, and combinations thereof. The imaging system 20 may also include a lens system, optical filters, collimators, diffusers, or any other optical-signal processing devices, for example. Further, the imaging system 20 is not limited to an optical imager in the visible spectrum, and may include an infrared imaging system, an ultra-violet imaging system, a microwave imaging system, an X-ray imaging system, and/or other desired imaging systems, for example. Non-exclusive examples of the imaging system 20 include optical imaging systems, spectrophotometers, gas chromatographs, microscopes, infrared sensors, and combinations thereof, for example.

In one embodiment, the imaging system 20 includes the camera 22 and a lens wherein the camera 22 is an OnSemi MT9D131 CMOS sensor (made by ON Semiconductor, Phoenix, Arizona) and the lens is a DSL949 Sunex lens (made by Sunex Inc., Carlsbad, CA), both configured to maintain a large field of view while keeping geometric image distortion low, thereby providing a resolution of 1600 pixels by 1200 pixels wherein each pixel depicts approximately a 0.065 mm square area of the sample tray 30 and/or the reagent test device 12 in the sample tray 30.

The mirror system 26 comprises the mirror 28 which is moveable between the first position to provide the first field of view and the second position to provide the second field of view. The first and second positions of the mirror 28 may be within the field of view of the imaging system 20. For example, the mirror 28 can be rotated or otherwise moved within the field of view to provide the first field of view and the second field of view. In some embodiments, the first position may be outside of the first field of view 40 of the imaging system 20. The second position may be inside the first field of view 40 of the imaging system 20, such that the second position is located between the imaging system 20 and the sample tray 30, and such that the mirror 28 intersects the first field of view 40. The mirror 28 in the second position may reflect light to produce the second field of view 42 to the imaging system 20 to capture the second image of the information indicator 18.

Though the second field of view 42 is shown in the figures as being outside of the sample tray 30, in some implementations, the first field of view 42 may encompass a first portion of the sample tray 30 (and thereby a first portion of the reagent test device 12 when in the sample tray 30) and the second field of view 42 may capture a second portion of the sample tray (and thereby a second portion of the reagent test device 12 when in the sample tray 30), such as when the information indicator 18 is located on the reagent test device 12.

In one embodiment, the mirror system 26 may comprise one or more mirror support 50 which may support the mirror 28 and/or move the mirror 28 between the first position to the second position. In one embodiment, the mirror system 26 may comprise one or more computer processor 48 or circuit board to send and receive signals to move the mirror 28 between the first position and the second position.

The sample tray 30 may have a sample holder 32 and may be configured to adjust the location of the sample holder 32 within the first field of view 40. The sample holder 32 may be configured to receive at least one of the reagent test device 12, such as a reagent strip, a lateral flow immunoassay test strip, a reagent card, and/or a reagent card cassette, each having a corresponding portion of the fluid sample 14.

In one embodiment, the sample holder 32 may be adapted to accept the reagent test device 12 in the form of a reagent card cassette having one or more multiple-profile reagent cards therein, for example. Each reagent card may include a substrate and one or more reagent pads positioned thereon, or otherwise associated therewith. In an exemplary embodiment, the reagent test device 12 may include fluidic or microfluidic compartments.

Each reagent test device 12 may include a reagent configured to undergo a color change in response to the presence of a target constituent such as a molecule, cell, or substance in the fluid sample 14 of a specimen deposited on the reagent test device 12. The reagent test device 12 may be provided with different reagents for detecting the presence of different target constituents. Different reagents may cause one or more color change in response to the presence of a certain constituent in the fluid sample 14, such as a certain type of analyte. The color developed by a reaction of a particular constituent with a particular reagent may define a characteristic discrete spectrum for absorption and/or reflectance of light for that particular constituent. The extent of color change of the reagent and the fluid sample 14 may depend on the amount of the target constituent present in the fluid sample 14, for example.

In particular, the reflectance value of the reagent test device 12 changes when the reagent test device 12 is wettened with the fluid sample 14. For a negative solution, the change in value is known (or can be measured) and therefore may become an optional offset value. Any change outside of the offset value is likely caused by a reaction with a clinical component (target constituent) that is being measured in the fluid sample 14.

The presence and concentrations of these target constituents in the fluid sample 14 may be determinable by an analysis of the color changes undergone by the one or more reagent test device 12 at predetermined times after application of the fluid sample 14 to the reagent test device 12 and/or at predetermined read positions in the first field of view 40 of the imaging system 20, for example. This analysis may involve a color comparison of each reagent test device 12 to itself at different time periods after application of the fluid sample 14 and/or at different read positions in the first field of view 40 of the imaging system 20.

Based upon an analysis of a magnitude of the optical signal detected by the imaging system 20, the fluid sample 14 may be assigned to one of a number of categories, e.g., a first category corresponding to no target constituent present in the fluid sample 14, a second category corresponding to a small concentration of target constituent present in the fluid sample 14, a third category corresponding to a medium concentration of target constituent present in the fluid sample 14, and a fourth category corresponding to a large concentration of target constituent present in the fluid sample 14, for example.

Further, the imaging system 20 may detect an optical signal indicative of a color or a reflectance value of the reagent test device 12 at any time interval after a volume of a portion of the fluid sample 14 has been dispensed on the reagent test device 12, e.g., the reagent pad and/or test strip, and regardless of location of the particular reagent test device 12, for example. In one exemplary embodiment, a video, or a sequence of images may be captured of the reagent test device 12 at a variety of time intervals after the volume of the portion of the fluid sample 14 is deposited on the reagent test device 12.

The imaging system 20 may be operated intermittently, continuously, or periodically, to detect one or more reflectance signals indicative of the color or the reflectance value of the one or more reagent test devices 12, e.g., reagent pads, at any time and at any position in the first field of view 40 of the camera 22, for example. In some exemplary embodiments, the imaging system 20 may capture the first image indicative of the color or the reflectance value of the reagent test device 12, e.g., the reagent pad, prior to any of the fluid sample 14 being deposited onto the reagent test device 12, or at any known time after a volume of the portion of the fluid sample 14 has been deposited onto the reagent test device 12, for example.

In some exemplary embodiments, the first image of the one or more reagent test device 12 may be taken by the imaging system 20 concurrently with dispensing the volume of the portion of the fluid sample 14 on the one or more reagent test device 12, before dispensing the volume of the portion of the fluid sample 14 on the one or more reagent test device 12, immediately after dispensing the volume of the portion of the fluid sample 14 on the one or more reagent test device 12, at a preset time after the volume of the portion of the fluid sample 14 is dispensed on the one or more reagent test device 12, and/or combinations thereof. In one exemplary embodiment, a video, or a sequence of the first images may be taken of the one or more reagent test device 14 as the one or more reagent test device 12 is advanced within the reagent analyzer 10 and as a volume of the portion of the fluid sample 14 is deposited on the one or more reagent test device 12.

The illumination source 34 may be implemented as one or more of a light emitting diode, a light bulb, a laser, an incandescent bulb or tube, a fluorescent light bulb or tube, a halogen light bulb or tube, or other light source or object configured to emit an optical signal having a predetermined intensity, wavelength, frequency, or direction of propagation, for example. In one embodiment, the one or more illumination source 34 may be a plurality of light emitting diodes and/or one or more IR LED. The illumination source 34 may produce a substantially uniform light intensity across the sample holder 32 and/or reagent test device(s) 12. In one embodiment, the illumination source 34 may be used to apply heat to the fluid sample 14. In one embodiment, the plurality of LEDs may be selected to provide a fixed color, visible light, ultra-violet light, infrared light, or white light, or some combination thereof.

Figure 5:
FIG. 5 is a top plan view of an exemplary reagent test device in accordance with the present disclosure.

Referring now to FIG. 5, shown therein is a portion of one embodiment of an exemplary reagent test device 12*a* in the form of a reagent card that can be read by the reagent analyzer 10 according to the inventive concepts disclosed herein.

The reagent card may include a substrate 128 and one or more, or a plurality of reagent pads 132*a-n* positioned thereon, or otherwise associated therewith. The substrate 128 may be constructed of any suitable material, such as paper, photographic paper, polymers, fibrous materials, and combinations thereof, for example. The reagent pads 132*a-n* may be arranged in a grid-like configuration on the substrate 128 so as to define one or more test strip, for example. In an exemplary embodiment, the reagent pads 132*a-n* may include fluidic or microfluidic compartments (not shown). The reagent pads 132*a-n* may be spaced apart a distance from one another so that the test strips are spaced apart such that adjacent test strips and/or reagent pads 132*a-n* may be simultaneously positioned at separate positions within the first field of view 40 of the imaging system 20, for example. The reagent card may be a multiple-profile reagent card having multiple reagent pads 132*a-n* having different reagents and/or multiple different test strips. Further, in some exemplary embodiments, the reagent card may include one or more calibration chips or reference pads, which may have no reagent and may serve as color references, for example. In some implementations, the reagent card may include an information indicator 18 having calibration information for the reagent analyzer 10 regarding the fluid sample 14 applied to the plurality of reagent pads 132*a-n* (FIG. 3).

Each reagent pad 132*a-n* may include a reagent configured to undergo a color change in response to the presence of a target constituent such as a molecule, cell, or substance in the fluid sample 14 of a specimen deposited on the reagent pad 132*a-n*. The reagent pads 132*a-n* may be provided with different reagents for detecting the presence of different target constituents. Different reagents may cause one or more color change in response to the presence of a certain constituent in the fluid sample 14, such as a certain type of analyte. The color developed by a reaction of a particular constituent with a particular reagent may define a characteristic discrete spectrum for absorption and/or reflectance of light for that particular constituent. The extent of color change of the reagent and the fluid sample 14 may depend on the amount of the target constituent present in the fluid sample 14, for example.

The color change may be read by the imaging system 20. In one embodiment, signals indicative of, or the first image depicting, the color of the reagent pads 132*a-n* may be received by the imaging system 20, which may analyze the signals and/or the first image and determine a change in the color of the reagent pad 132*a-n* as a result of the reagent pad 132*a-n* reacting with the volume of the fluid sample 14 deposited thereon. Such color change may be analyzed as a function of the read position of the reagent pad 132*a-n* when the optical signal or the first image indicative of the color of the reagent pad 132*a-n* was detected and/or as a function of the known duration of time the volume of the fluid sample 14 has been deposited onto the reagent pad 132*a-n*, and/or combinations thereof, for example. The color change may be interpreted as a quantitative, qualitative, and/or semi-qualitative indication of the presence and/or concentration or amount of a target constituent in the volume of the fluid sample 14 deposited on the reagent pad 132a-n as described above.

Figure 6:
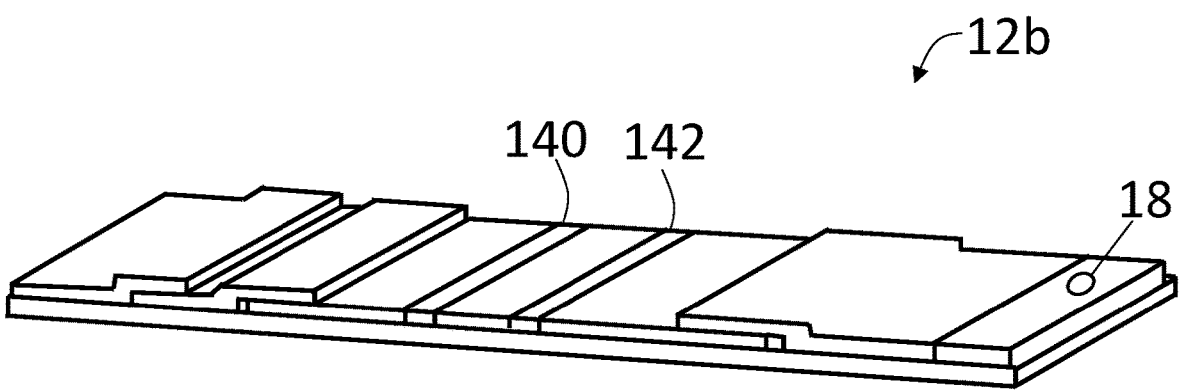
FIG. 6 is a perspective view of another exemplary reagent test device in accordance with the present disclosure.

Referring now to FIG. 6, shown therein is a portion of one embodiment of an exemplary reagent test device 12b in the form of a lateral flow immunoassay test strip that can be read by the reagent analyzer 10 according to the inventive concepts disclosed herein. The reagent test device 12b may include a test line 140 that provides the result of the test by showing, or not showing, a visible line, and a control line 142 which confirms the test is working properly. The reagent test device 12b may have a flow path which conveys the fluid sample 14 past the test line 140 and the control line 142. In some implementations, the reagent test device 12b may include the information indicator 18.

Referring again to FIGS. 1-3, the analyzer system 100 may further comprise an analyzer controller 144. The analyzer controller 144 may comprise one or more computer processor 148 (which may be referred to simply as processor 148) and one or more non-transitory computer readable memory 152 (which may be referred to as one or more non-transitory computer readable medium 152, non-transitory memory 152, or simply as memory 152). The analyzer controller 144 may further comprise one or more database 156. The memory 152 may store computer executable instructions (also referred to as code or software) that, when executed by the processor 148, causes the processor 148 to communicate with and/or be operable coupled to other elements of the reagent analyzer 10. Exemplary non-transitory computer readable memory 152 may include random access memory, read only memory, flash memory, and/or the like. Such non-transitory computer readable mediums may be electrically based, optically based, and/or the like.

The processor 148 may be a single processor or multiple processors working independently or together to collectively perform one or more task. Exemplary embodiments of the processor 148 include a digital signal processor (DSP), a central processing unit (CPU), a field programmable gate array (FPGA), a microprocessor, a multi-core processor, and/or combinations thereof. The processor 148 may be capable of communicating with the memory 152 via a path (e.g., data bus). The processor 148 may be capable of reading and/or executing processor executable code and/or of creating, manipulating, altering, and/or storing computer data structures into the non-transitory memory 152. The processor(s) 148 may or may not necessarily be located in a single physical location. In one embodiment, the non-transitory memory 152 stores program logic, for example, a set of instructions capable of being executed by the processor 148, that when executed by the processor 148 causes the processor 148 to carry out the methods disclosed herein.

While the analyzer controller 144 is depicted separately from the reagent analyzer 10, it is understood that in some embodiments, the analyzer controller 144 may be integrated into the reagent analyzer 10, such as, by way of example only, the analyzer controller 144 may be an additional component of the reagent analyzer 10 or may be integrated with another component of the reagent analyzer 10.

In one embodiment, the imaging system 20 may be operably coupled with the analyzer controller 144 and/or the processor 148 so that one or more power and/or control signals may be transmitted to the camera 22, the mirror system 26, and/or to the one or more illumination source 34 by the controller 144, and so that one or more signals may be transmitted from the camera 22 and/or the imaging system 20 to the processor 148, for example.

In one embodiment, the mirror system 26 may be operably coupled with the analyzer controller 144 and/or the processor 148 so that one or more power and/or control signals may be transmitted to one or more of the mirror support 50 and/or the mirror 28, such as to move the mirror 28 between the first position to the second position.

The analyzer controller 144 may be configured to gauge test results as the reagent test device 12 is sampled within the reagent analyzer 10, for example, by receiving one or more signals and/or the first image from the camera 22. The camera 22 may be configured to detect or capture one or more optical or other signals indicative of a reflectance value of the reagent test device 12, such as a reagent pad, and to transmit a signal indicative of the reflectance value of the reagent test device 12, e.g., the reagent pad, to the processor 118, for example.

One or more optical signals having wavelengths indicative of a reflectance value of the reagent pads and/or the test strip may be detected by the camera 22 at one or more read position, for example. The camera 22 may detect an optical signal indicative of a reflectance value of a reagent pad and/or test strip at any desired read position, location, or area within the first field of view 40, or any other desired location or area or multiple locations or areas, for example. The signal transmitted to the processor 148 by the camera 22 may be an electrical signal, an optical signal, and combinations thereof, for example. In one embodiment, the signal is in the form of a first image file for the first image, the first image file having a matrix of pixels, with each pixel having a color code indicative of a reflectance value. In an exemplary embodiment, the first image file may have two or more predetermined regions of pixels, each predetermined region of pixels corresponding to a read position of one of the reagent pads and/or the test strip in the field of view 40 of the camera 22. In one embodiment, the processor 148 may store the signal transmitted and or the first image file in one or more database 156 and/or in the memory 152.

The processor 148 may determine the reflectance value or the color change of the reagent test device 12, such as a reagent pad and/or a test strip, along with the fluid sample 14 (e.g., urine) disposed on the reagent test device 12 based on the signals detected by the camera 22, for example. Each optical or other signal indicative of one or more reflectance value readings detected by the camera 126 may have a magnitude relating to a different wavelength of light (i.e., color). The color of the fluid sample(s) 14 and/or the reaction of the one or more reagents with a target constituent in the reagent test device 12 may be determined based upon the relative magnitudes of the reflectance signals of various color components, for example, red, green, and blue reflectance component signals. For example, the color of each reagent test device 12 may be translated into a standard color model, which typically includes three or four values or color components (e.g., Red-Green-Blue (RGB) color model, including hue, saturation, and lightness (HLS) and hue, saturation, and value (HSV) representation of points and/or CMYK color model, or any other suitable color model) whose combination represents a particular color. In some embodiments, the camera 22 may detect multiple optical signals at each read position, with each detected signal having one or more color components, such as a red component signal, a green component signal, and a blue component signal, for example, and each of the component signals may be transmitted to the processor 148. In some exemplary embodiments, the camera 22 may detect a single optical signal at each read position, and the processor 148 may translate a signal received from the camera 22 into separate color component signals such as a red component signal, a green component signal, and a blue component signal, for example.

The processor 148 may analyze the second image, and/or optical signals, depicting the information indicator 18, which may be referred to as the information image, from the imaging system 20. The second image (i.e., the information image) comprises pixels and depicts the information indicator 18. The processor 148 may determine calibration information and/or identification information, stored in the information indicator 18, for the fluid sample 14. The processor 148 may utilize the determined calibration information to analyze the second image depicting the reagent test device 12 with the fluid sample applied to the reagent test device 12.

In some implementations, the information indicator 18 may be indicative of one or more of the following data: coefficients that may be utilized to change the RGB value ranges that correspond to a specific analyte value; region information for region-specific reagents which give specific units in the result or ensure that the reagent can be run in that region/country; expiry information (for example, in the case of shelf life limitations); temperature excursion information (for example, to make sure the reagent is valid); and/or identification of the reagent type (for example, so that different similar looking reagent cassettes/strips can be used without user selection). It is contemplated that the information indicator 18 may be indicative of additional or other data.

In one embodiment, the processor 148 may execute processor executable code stored in the non-transitory memory 152 that causes the processor 148 to receive or obtain the first image and the second image, to determine one or more reflectance value or the color change of the reagent test device 12, and/or to determine the calibration information, and/or identification information, and/or other information, stored in the information indicator 18 for the fluid sample 14.

Figure 7:
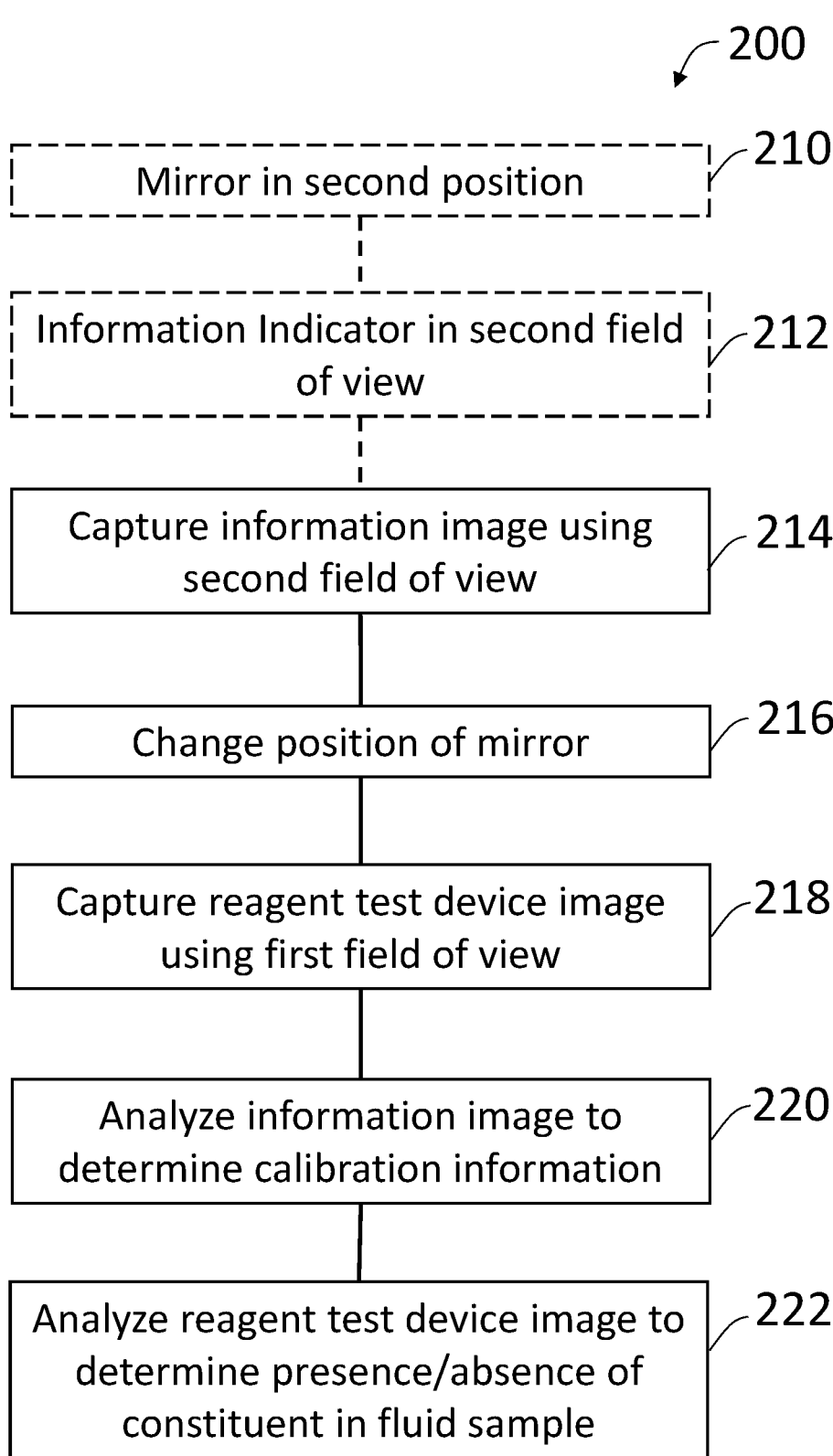
FIG. 7 is a process flow diagram of an exemplary method of use of an exemplary analyzer system in accordance with the present disclosure.

Referring now to FIG. 7, a method of use of the analyzer system 200 will now be described. In a step 210, the mirror 28 of the mirror system 26 may be moved from the first position to the second position. The first position may be outside of the first field of view 40 of the imaging system 20. The second position may be inside the first field of view 42 of the imaging system 20, the second position located between the imaging system 20 and the sample tray 30 configured to hold the reagent test device 12 with a portion of the fluid sample 14 applied to the reagent test device 12. The second position may be inside the first field of view 42 of the imaging system 20, the second position located between the imaging system 20 and the reagent test device 12. When in the second position, the mirror 28 may be positioned to reflect light to produce the second field of view 42 to the imaging system 20. Of course, it will be understood that the mirror 28 may start in the second position such that no movement is required to reach the second position, and may be moved to the first position.

In an optional step 212, the information indicator 18 of the sample vessel 16 containing the fluid sample 14 may be moved to a position in the second field of view 42 of the imaging system 20, the information indicator 18 indicative of calibration information for use with testing the fluid sample 14 and/or the information indicator 18 indicative of identification or other information for the fluid sample 14. In one embodiment, the information indicator 18 may be located on the reagent test device 12, and the information indicator 18 of the reagent test device 12 may be positioned in the second field of view 42 of the imaging system 20 (see FIG. 3) before testing of the reagent test device 12.

The information indicator 18 may be positioned automatically or manually in the second field of view 42. Of course, it will be understood that the information indicator 18 of the sample vessel 16 and/or the reagent test device 12 may already be in position in the second field of view 42.

In one embodiment, a portion of the reagent test device 12 having the information indicator 18 may be encompassed by the second field of view 42, while another portion of the reagent test device 12 may be encompassed by the first field of view 40.

In a step 214, the imaging system 20 may capture, using the second field of view 42, the information image. The information image comprises pixels and depicts the information indicator 18 of the sample vessel 16.

In a step 216, the mirror 24 may be moved from second position to the first position.

In a step 218, the reagent test device 12 may be positioned in the sample tray 30 (such as in the sample holder 32) in the first field of view 40 of the imaging system 20 and the imaging system 20 may capture, using the first field of view 40, the first image (i.e. the device image). The device image has pixels and depicts at least a portion of the reagent test device 12.

In a step 220, the processor 148 may execute processor executable code stored in the non-transitory computer readable medium 152, to analyze the pixels of the information image to determine the calibration information and/or identification information for the fluid sample 14 from the information indicator 18.

In a step 222, the processor 148 may execute processor executable code stored in the non-transitory computer readable medium 152, to analyze the pixels of the device image to determine a presence or an absence of a target constituent being in the fluid sample 14 applied to the reagent test device 12, using, in part, the determined calibration information and/or other information from the information indicator 18.

In one embodiment, the processor 148 may calculate a calibration factor for each reagent pad at each read position by selecting or otherwise designating a reagent pad as a reference reagent pad and referencing each of the remaining reagent pad to the reference reagent pad based on a ratio of the reflectance values of the optical signal or image detected at the reference reagent pad to the respective optical signals or images detected at each reagent test device 12 (such as a reagent pad) by the camera 22. In some embodiments, the calibration factor may be utilized to calibrate out the variations in color intensity due to illumination or other factors in a specific setting. Further, in some exemplary embodiments, rather than selecting a reference reagent pad, each reagent pad may be referenced to an ideal color or to a color standard for each reagent pad, as will be appreciated by persons of ordinary skill in the art.

In some implementations, a calibration routine may be implemented as a set of processor executable instructions or logic stored in the non-transitory computer readable medium 152, which instructions or logic when executed by the processor 148, cause the processor 148 to carry out the logic to calculate or determine the calibration factors. The calibration routine may be carried out periodically, such as at a preset interval of time, with each new lot of reagent cards, as desired according to specific quality control procedures applicable to the reagent analyzer 10, and combinations thereof, for example.

In the calibration routine, the camera 22 may detect a first optical signal or a first image indicative of the reflectance value of a calibration test strip positioned within the sample holder 32. The calibration test strip may be a dry reagent card having one or more dry reagent pads. Each image may include metadata stored into the image such as a power level for the illumination source 34. Because the calibration test strip does not have a sample deposited thereon, a reaction is not occurring, and the color of the calibration test strip should be uniform across the calibration test strip. Thus, differences in the reflectance values detected in the first image and second image are due to non-uniform illumination.

The camera 22 may detect a test optical signal or obtain a test image indicative of the reflectance value of the calibration test strip positioned within the sample holder 32, for example. The camera 22 may detect the test image having a region of pixels having color or reflectance values depicting the color of the calibration test strip, and transmit such image to the processor 148.

The following is a number list of non-limiting illustrative embodiments of the inventive concept disclosed herein:

1. A reagent analyzer, comprising:
   a sample tray configured to hold a reagent test device with a portion of a fluid sample applied to the reagent test device;
   an imaging system having a first field of view and a second field of view, the first field of view encompassing at least a portion of the reagent test device held in the sample tray, the second field of view encompassing an information indicator, the imaging system configured to capture a first image having pixels using the first field of view and to capture a second image having pixels using the second field of view, the first image depicting at least a portion of the reagent test device and the second image depicting the information indicator;
   a mirror moveable between a first position to provide the first field of view and a second position to provide the second field of view, the second position located between the imaging system and the sample tray, the mirror in the second position reflecting light to produce the second field of view to the imaging system to capture the second image; and
   a computer processor executing instructions that cause the computer processor to:
      receive the first image and the second image;
      analyze the pixels of the first image to determine calibration information from the information indicator for analyzing the fluid sample; and
      analyze the pixels of the second image to determine a presence or an absence of a target constituent being in the fluid sample applied to the reagent test device, using, in part, the determined calibration information.
2. The reagent analyzer of illustrative embodiment 1, wherein the information indicator is located on the reagent test device.
3. The reagent analyzer of illustrative embodiment 1, wherein the information indicator is located on a sample vessel for the fluid sample.
4. The reagent analyzer of any one of illustrative embodiments 1-3, wherein the information indicator comprises one or more of: a one-dimensional barcode, a two-dimensional barcode, an alphanumeric character, an icon, and a chemical indicator.
5. The reagent analyzer of any one of illustrative embodiments 1-4, wherein the calibration information comprises one or more of: coefficients that may be utilized to change RGB value ranges that correspond to a specific analyte value, geographic region information, expiry information, temperature excursion information, coefficients for use in conversion of measured image values into analytical results, chemical information, and identification of reagent type.
6. The reagent analyzer of any one of illustrative embodiments 1-5, wherein the first field of view is different than the second field of view.
7. The reagent analyzer of any one of illustrative embodiments 1-6, wherein the first field of view does not overlap the second field of view.
8. The reagent analyzer of any one of illustrative embodiments 1-6, wherein the first field of view partially, but not completely, overlaps the second field of view.
9. A method, comprising:
   moving a mirror from a first position to a second position, the first position providing a first field of view of an imaging system and the second position providing the second field of view of the imaging system, the second position located between the imaging system and a sample tray configured to hold a reagent test device with a portion of a fluid sample applied to the reagent test device, the mirror in the second position reflecting light to produce a second field of view to the imaging system;
   capturing, with the imaging system using the second field of view, an information image having pixels, the information image depicting an information indicator indicative of calibration information for use in analyzing the fluid sample;
   moving the mirror from the second position to the first position;
   capturing, with the imaging system using the first field of view, a device image having pixels, the device image depicting at least a portion of the reagent test device;
   analyzing, with a computer processor executing processor executable code stored in a non-transitory computer readable medium, the pixels of the information image to determine the calibration information for the fluid sample from the information indicator; and
   analyzing, with the computer processor executing processor executable code stored in a non-transitory computer readable medium, the pixels of the device image to determine a presence or an absence of a target constituent being in the fluid sample applied to the reagent test device, using, in part, the determined calibration information.
10. The method of illustrative embodiment 9, wherein the information indicator is located on one or more of the reagent test device and a sample vessel for the fluid sample.
11. The method of any one of illustrative embodiments 9-10, wherein the information indicator comprises one or more of: a one-dimensional barcode, a two-dimensional barcode, an alphanumeric character, an icon, and a chemical indicator.
12. The method of any one of illustrative embodiments 9-11, wherein the calibration information comprises one or more of: coefficients that may be utilized to change RGB value ranges that correspond to a specific analyte value, geographic region information, expiry information, temperature excursion information, coefficients for use in conversion of measured image values into analytical results, chemical information, and identification of reagent type.

US 12,596,130 B2

19

13. A reagent analyzer, comprising:
an imaging system having a first field of view and a
second field of view, the first field of view positioned
to encompass at least a portion of a reagent test device,
the second field of view positioned to encompass an
information indicator of a fluid sample, the imaging
system configured to capture a first image having pixels
using the first field of view and to capture a second
image having pixels using the second field of view, the
first image depicting at least a portion of the reagent test
device and the second image depicting the information
indicator;
a mirror moveable between a first position to provide the
first field of view of the imaging system and a second
position to provide the second field of view of the
imaging system, the second position located between
the imaging system and the reagent test device, the
mirror in the second position reflecting light to produce
the second field of view to the imaging system to
capture the second image; and
a computer processor executing instructions that cause the
computer processor to:
receive the first image and the second image;
analyze the pixels of the first image to determine
calibration information from the information indica-
tor for analyzing the fluid sample; and
analyze the pixels of the second image to determine a
presence or an absence of a target constituent being
in the fluid sample applied to the reagent test device,
using, in part, the determined calibration informa-
tion.
14. The reagent analyzer of illustrative embodiment 13,
wherein the information indicator is located on the
reagent test device.
15. The reagent analyzer of illustrative embodiment 13,
wherein the information indicator is located on a
sample vessel for the fluid sample.
16. The reagent analyzer of illustrative embodiment 13,
wherein the information indicator comprises one or
more of: a one-dimensional barcode, a two-dimen-
sional barcode, an alphanumeric character, an icon, and
a chemical indicator.
17. The reagent analyzer of illustrative embodiment 13,
wherein the calibration information comprises one or
more of: coefficients that may be utilized to change
RGB value ranges that correspond to a specific analyte
value, geographic region information, expiry informa-
tion, temperature excursion information, coefficients
for use in conversion of measured image values into
analytical results, chemical information, and identifi-
cation of reagent type.
18. The reagent analyzer of illustrative embodiment 13,
wherein the first field of view is different than the
second field of view.
19. The reagent analyzer of illustrative embodiment 13,
wherein the first field of view does not overlap the
second field of view.
20. The reagent analyzer of illustrative embodiment 13,
wherein the first field of view partially, but not com-
pletely, overlaps the second field of view.
21. A reagent analyzer, comprising:
a sample tray configured to hold a reagent test device with
a portion of a fluid sample applied to the reagent test
device;
an imaging system having a first field of view and a
second field of view, the first field of view encompass-
ing at least a portion of the reagent test device held in the sample tray, the second field of view encompassing
an information indicator, the imaging system config-
ured to capture a first image having pixels using the first
field of view and to capture a second image having
pixels using the second field of view, the first image
depicting at least a portion of the reagent test device
and the second image depicting the information indi-
cator; and
a computer processor executing instructions that cause the
computer processor to:
receive the first image and the second image;
analyze the pixels of the first image to determine
calibration information from the information indica-
tor for analyzing the fluid sample; and
analyze the pixels of the second image to determine a
presence or an absence of a target constituent being
in the fluid sample applied to the reagent test device,
using, in part, the determined calibration informa-
tion.
22. The reagent analyzer of illustrative embodiment 21,
wherein the information indicator is located on the
reagent test device.
23. The reagent analyzer of illustrative embodiment 21,
wherein the information indicator is located on a
sample vessel for the fluid sample.
24. The reagent analyzer of any one of illustrative
embodiments 21-23, wherein the information indicator
comprises one or more of: a one-dimensional barcode,
a two-dimensional barcode, an alphanumeric character,
an icon, and a chemical indicator.
25. The reagent analyzer of any one of illustrative
embodiments 21-24, wherein the calibration informa-
tion comprises one or more of: coefficients that may be
utilized to change RGB value ranges that correspond to
a specific analyte value, geographic region information,
expiry information, temperature excursion information,
coefficients for use in conversion of measured image
values into analytical results, chemical information,
and identification of reagent type.
26. The reagent analyzer of any one of illustrative
embodiments 1-5, wherein the first field of view is
different than the second field of view.
27. The reagent analyzer of any one of illustrative
embodiments 21-26, wherein the first field of view does
not overlap the second field of view.
28. The reagent analyzer of any one of illustrative
embodiments 21-26, wherein the first field of view
partially, but not completely, overlaps the second field
of view.
Further, as will be appreciated by persons of ordinary skill
in the art, the calibration routine may be carried out on one
or more calibration test strips on a reagent card and the
remaining test strips may be used to test a sample as
described above to reduce the downtime for the reagent
analyzer 10, for example. In one embodiment, the reagent
analyzer 10 may determine a non-uniformity value before
the sample is analyzed to confirm current calibration. If the
reagent analyzer 10 is determined to be uncalibrated, the
calibration routine may be performed.
It is to be understood that the steps disclosed herein may
be performed simultaneously or in any desired order. For
example, one or more of the steps disclosed herein may be
omitted, one or more steps may be further divided in one or
more sub-steps, and two or more steps or sub-steps may be
combined in a single step, for example. Further, in some
exemplary embodiments, one or more steps may be repeated
one or more times, whether such repetition is carried out sequentially or interspersed by other steps or sub-steps. Additionally, one or more other steps or sub-steps may be carried out before, after, or between the steps disclosed herein, for example.

It is to be understood that while the inventive concepts disclosed herein are described in connection with detecting a reflectance value of reagent pads, in some exemplary embodiments of the instant inventive concept, an absorbance value, a transmittance value, or any other value or property relating to a color or a color change of a reagent pad may be used to calculate calibration.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

What is claimed is:

1. A reagent analyzer, comprising:
   a sample tray configured to hold a reagent test device with a portion of a fluid sample applied to the reagent test device;
   an imaging system having a first field of view and a second field of view, the first field of view encompassing at least a portion of the reagent test device held in the sample tray, the second field of view encompassing an information indicator, the imaging system configured to capture a first image having pixels using the first field of view and to capture a second image having pixels using the second field of view, the first image depicting at least a portion of the reagent test device and the second image depicting the information indicator;
   a mirror moveable between a first position to provide the first field of view and a second position to provide the second field of view, the second position located between the imaging system and the sample tray, the mirror in the second position reflecting light to produce the second field of view to the imaging system to capture the second image; and
   a computer processor executing instructions that cause the computer processor to:
      receive the first image and the second image;
      analyze the pixels of the second image to determine calibration information from the information indicator for analyzing the fluid sample; and
      analyze the pixels of the first image to determine a presence or an absence of a target constituent being in the fluid sample applied to the reagent test device, using, in part, the determined calibration information.

2. The reagent analyzer of claim 1, wherein the information indicator is located on the reagent test device.

3. The reagent analyzer of claim 1, wherein the information indicator is located on a sample vessel for the fluid sample.

4. The reagent analyzer of claim 1, wherein the information indicator comprises one or more of: a one-dimensional barcode, a two-dimensional barcode, an alphanumeric character, an icon, and a chemical indicator.

5. The reagent analyzer of claim 1, wherein the calibration information comprises one or more of: coefficients that may be utilized to change RGB value ranges that correspond to a specific analyte value, geographic region information, expiry information, temperature excursion information, coefficients for use in conversion of measured image values into analytical results, chemical information, and identification of reagent type.

6. The reagent analyzer of claim 1, wherein the first field of view is different than the second field of view.

7. The reagent analyzer of claim 1, wherein the first field of view does not overlap the second field of view.

8. The reagent analyzer of claim 1, wherein the first field of view partially, but not completely, overlaps the second field of view.

* * * * *